(12) United States Patent
Mayrhofer et al.

(10) Patent No.: US 6,972,029 B2
(45) Date of Patent: Dec. 6, 2005

(54) HEALING GARMENT

(76) Inventors: Patricia Mayrhofer, 47 Great Oak Dr., Churchville, PA (US) 18966; Ivy Abendroth, 408A Avenue E., Horsham, PA (US) 19044

( * ) Notice: Subject to any disclaimer, the term of this patent is extended or adjusted under 35 U.S.C. 154(b) by 0 days.

(21) Appl. No.: 10/683,332

(22) Filed: Oct. 10, 2003

(65) Prior Publication Data

US 2005/0075706 A1  Apr. 7, 2005

Related U.S. Application Data

(60) Provisional application No. 60/417,424, filed on Oct. 10, 2002.

(51) Int. Cl.⁷ .............................................. A61F 7/00
(52) U.S. Cl. ................. 607/114; 607/108; 607/109; 607/112
(58) Field of Search ..................................... 607/114

(56) References Cited

U.S. PATENT DOCUMENTS

| 5,072,598 A | * | 12/1991 | Dibrell ..................... 62/259.3 |
| 5,086,629 A | * | 2/1992 | Dibrell ..................... 62/259.3 |
| 5,265,669 A | * | 11/1993 | Schneider .................. 165/46 |
| 5,302,806 A | | 4/1994 | Simmons et al. |
| 5,395,399 A | * | 3/1995 | Rosenwald ................ 607/108 |
| 5,697,962 A | * | 12/1997 | Brink et al. .............. 607/108 |
| 5,733,321 A | * | 3/1998 | Brink ....................... 607/111 |
| 5,826,273 A | | 10/1998 | Eckes |
| 5,890,487 A | | 4/1999 | Kimmel |
| D421,329 S | | 3/2000 | Adams |
| 6,185,744 B1 | | 2/2001 | Poholski |
| 6,189,149 B1 | | 2/2001 | Allen |
| 6,329,638 B1 | | 12/2001 | Bloodworth |
| 6,582,383 B2 | * | 6/2003 | Horning .................... 602/60 |
| 2001/0018604 A1 | | 8/2001 | Elkins |
| 2001/0037076 A1 | | 11/2001 | Shelton |

* cited by examiner

Primary Examiner—Henry M Johnson, III
(74) Attorney, Agent, or Firm—Akin Gump Strauss Hauer & Feld, LLP

(57) ABSTRACT

A garment for warming, cooling or maintaining the temperature of a specific area of a user's body includes a hoop-shaped support structure, at least one pocket on the support structure and at least one mass. The mass is removably positionable in the at least one pocket. The garment is worn by a user such that the at least one pocket is positioned adjacent the specific area of the user's body in a working position.

12 Claims, 3 Drawing Sheets

HEALING GARMENT

CROSS-REFERENCE TO RELATED APPLICATIONS

This application claims the benefit of U.S. Provisional Patent Application 60/417,424, filed Oct. 10, 2002, entitled "Healing Garment".

BACKGROUND OF THE INVENTION

The present invention is directed to a garment for warming a specific area of a user's body and, more particularly, to a healing garment that is worn by a user such that a pocket on the garment that holds a heated stone is positioned adjacent a user's body to improve energy flow and muscle relaxation, without requiring the attention of a massage technician.

It is known in the massage arts that the strategic placement of heated stones on the body may improve energy flow and relaxation of a patient during a massage. The application of a constant heat or temperature to tight and stressed muscles or specific parts of a patient's body increases energy flow in the body, which promotes relaxation.

Massage techniques are used prior to or following a manicure or pedicure to relax a customer and to provide the full body treatment. However, because a single technician works with a single customer, either a massage or a manicure/pedicure is provided at any one time. Attention can only be given to a single area of a patient's body or to a particular technique at one time because the technician is physically able to work on only one portion of the patient's body. Massage technicians are similarly limited because the single technician is physically limited the number of tasks that can be performed at one time. Further, massage technicians suffer from fatigue and the quality and effectiveness of their massages may vary as the technician becomes fatigued.

BRIEF SUMMARY OF THE INVENTION

Briefly, the present invention is directed to a garment for warming a specific area of a user's body. The garment includes a hoop-shaped support structure with at least one pocket in the support structure. At least one mass is removably positionable in the at least one pocket. The garment is worn by a user such that the at least one pocket is positioned adjacent the specific area of the user's body that is to be warmed in a working position.

In another aspect, the present invention is directed to a garment for warming a specific area of a user's body. The garment includes a support structure with at least one pocket positioned on the support structure. At least one heated stone is removably positionable in the at least on pocket. The support structure is securable to a user's body such that the at least one pocket with the at least one heated stone located therein is positioned adjacent the specific area of the user's body in the working position.

In yet another aspect, the present invention is directed to a healing garment including at least one pocket. At least one heated mass may be placed into the at least one pocket. The garment is worn by a user such that the at least one pocket is positioned adjacent an area of the user's body where healing is desired.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
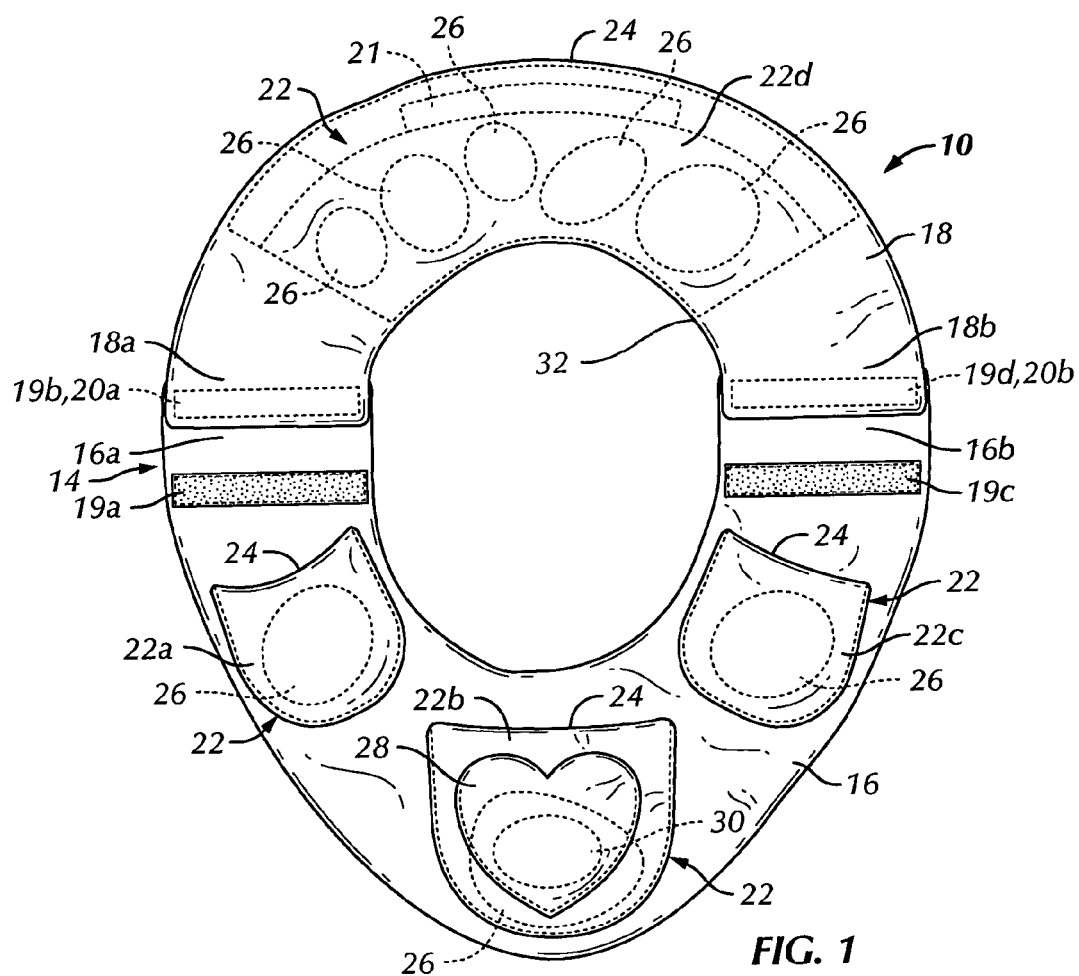
FIG. 1 is a front view of the healing garment in accordance with a preferred embodiment of the present invention.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the healing garment and designated parts thereof. The terminology includes the words above specifically mentioned, derivatives thereof and words of similar import.

Figure 2:
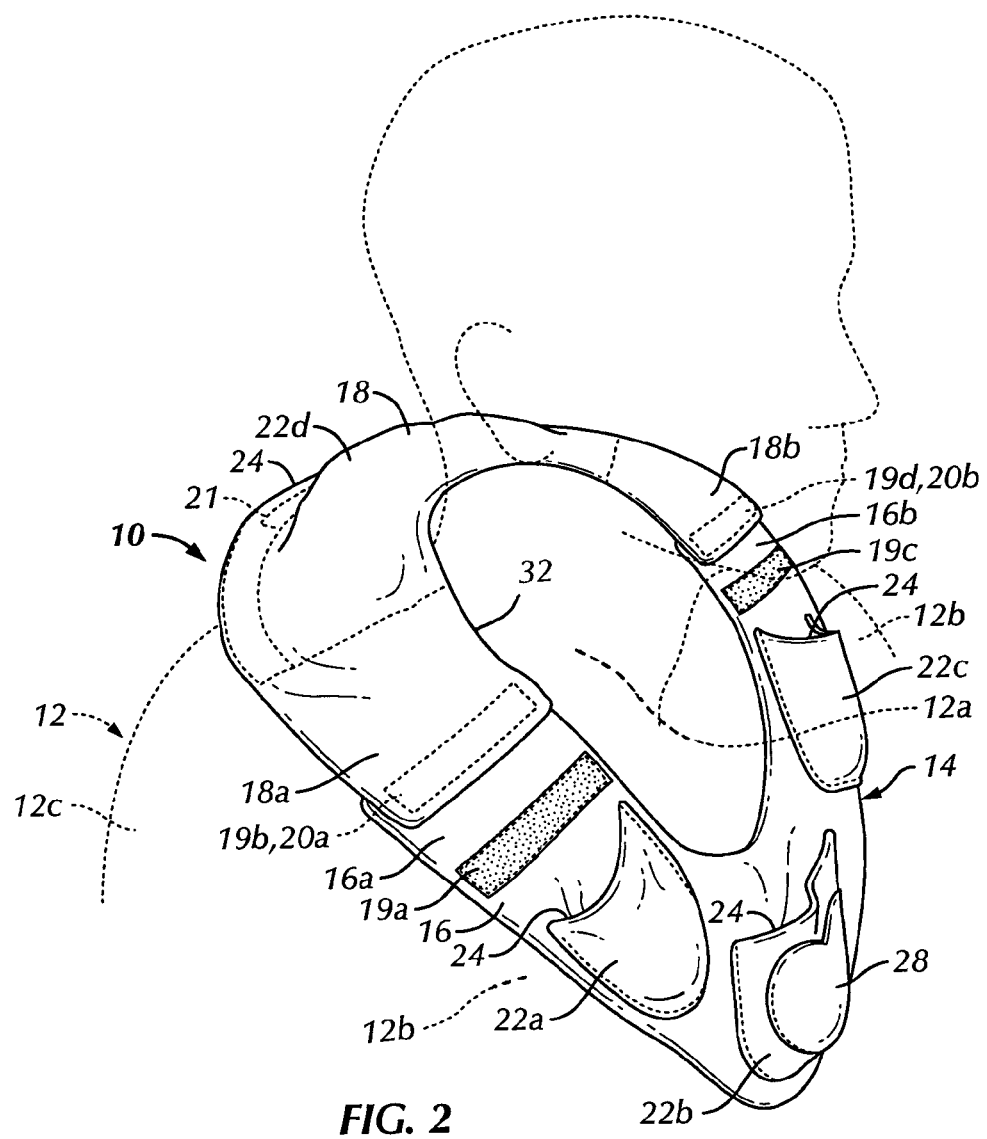
FIG. 2 is a left-side perspective view of the healing garment, shown in FIG. 1, positioned on a user in a working position.
Figure 3:
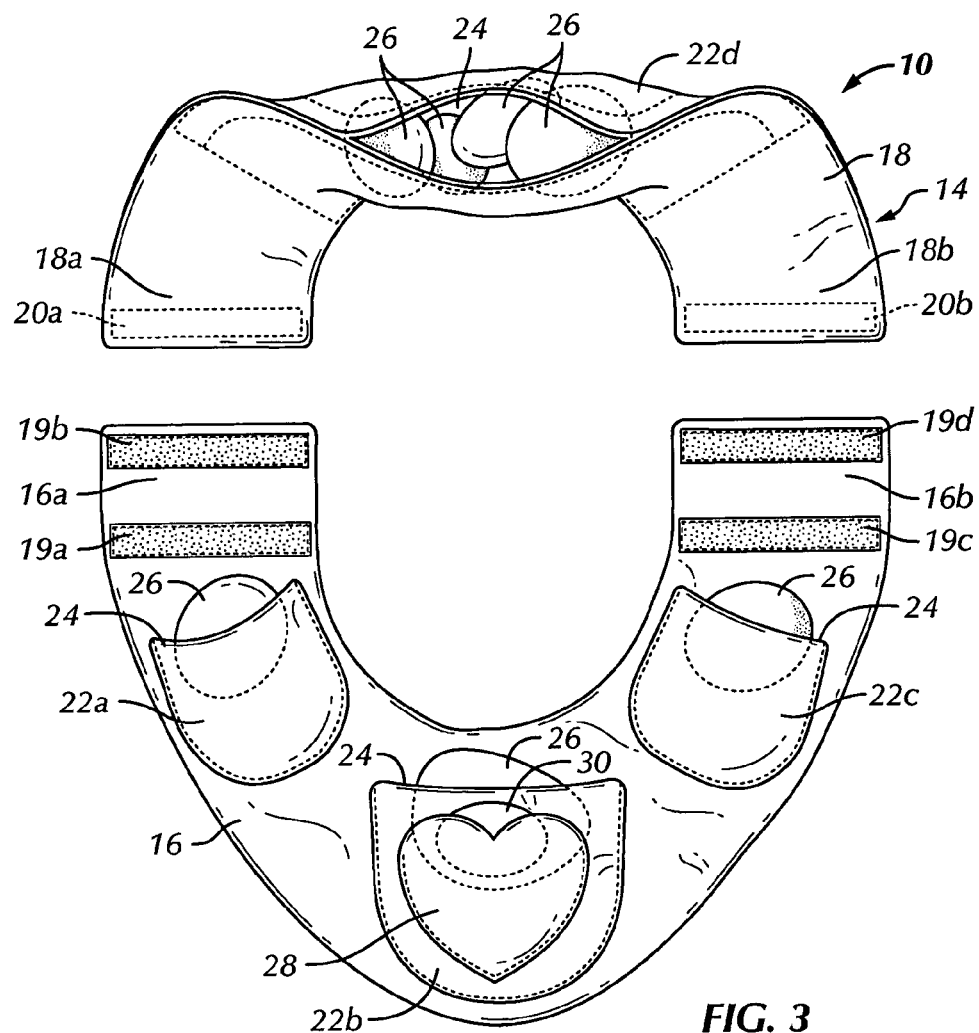
FIG. 3 is a front view of the healing garment, shown in FIG. 1, with a first and second garment section detached and the second garment section folded over to expose an open pocket of the second garment section.

Referring to the drawings in detail, wherein like numerals indicate like elements throughout, there is shown in FIGS. 1 through 3, a preferred embodiment of a healing garment, generally designated 10, in accordance with the present invention. The healing garment 10 is preferably used to warm a specific area of a user's body 12. However, the healing garment 10 is not limited to warming the user's body 12 and may be used to cool or hold a specific area of the user's body 12 at a relatively constant temperature. The remainder of the description of the garment 10 refers to heating specific areas of a user's body, however, the garment 10 may also be used to cool or hold specific areas of the user's body at a constant temperature in the same or substantially the same manner, described in greater detail below.

In a preferred embodiment, the garment 10 includes a hoop-shaped support structure 14 that is comprised of a first garment section 16 and a second garment section 18. Each of the garment sections 16, 18 form approximately one-half of the hoop-shaped support structure 14 of the garment 10 and have a generally U-shape. The garment sections 16, 18 are preferably, relatively wide and thin, such that a rear face of the garment sections 16, 18 rest firmly against the user's body 12 when in a working position. The support structure 14 is not limited to hoop-shaped constructions nor to constructions including the U-shaped first and second garment sections 16, 18. The support structure 14 may be formed in nearly any shape and may include single or multiple garment sections that permit the garment 10 to be placed onto a user's body 12 with a level of comfort and to come into contact with specific areas of a user's body 12 to be treated. For example, the garment 10 may be constructed of a single circular-shaped support structure 14 that is positioned around a neck 12a of the user's body 12 to heat the neck 12a, a single oval-shaped support structure 14 with two detachable ends to heat the neck 12a, back and chest 12b or in the shape of a vest having multiple garment sections to heat the back, chest 12b and/or and ribs (not shown). Other shapes or configurations of the support structure 14 will be apparent to one having ordinary skill in the art.

Preferably, the first garment section 16 includes first and second ends 16a, 16b and the second garment section 18 includes third and fourth ends 18a, 18b. The first and third ends 16a, 18a and the second and fourth ends 16b, 18b are removably securable to each other to form the preferred hoop-shaped support structure 14. The first and third ends 16a, 18a and the second and fourth ends 16b, 18b are removably securable to each other through securing strips 19a, 19b, 19c, 19d, 20a, 20b that are located on the first, second, third and fourth ends 16a, 16b, 18a, 18b. Specifically, in the preferred embodiment, first and second securing strips 19a, 19b are attached to the first garment section adjacent the first end 16a, third and fourth securing strips 19c, 19d are attached to the first garment section adjacent the second end 16b, a fifth securing strip 20a is attached to the third end 18a and a sixth securing strip 20b is attached to the fourth end 18b. The securing strips 19a–19d, 20a, 20b are comprised of hook and loop material in the preferred embodiment that is secured along a width of the ends 16a, 16b, 18a, 18b by an attachment device or method that is generally well known in the art. For example, stitching, adhesively bonding or clamping may be used to secure the securing strips 19a–19d, 20a, 20b to the garment sections 16, 18. The strips 19a–19d, 20a, 20b not limited to the hook and loop material to releasably secure the ends 16a, 16b, 18a, 18b together and may employ nearly any device or method that is able to secure the ends 16a, 16b, 18a, 18b relative to each other when the support structure 14 is in its working position. For example, the ends 16a, 16b, 18a, 18b may be secured to each other using zippers, buttons, snaps, clamps, adhesive strips or any attachment device that would removably secure the ends 16a, 16b, 18a, 18b relative to each other in the working position.

The size of a hole 32 in the center of the hoop-shaped support structure 14 may be altered in the preferred embodiment by connecting various pairs of the first, second, third and fourth strips 19a–19d to the fifth and sixth strips 20a, 20. Forming various sized hoop-shaped healing garments 10 is advantageous so that the size of the healing garment 10 may be adapted to various sized users and to alter the positioning of the garment 10 to apply heat to various areas on a user's body 12, as will be explained in greater detail below. Healing garments 10 having various other shapes, some of which were described above, may also include a plurality of strips or alternative attachment devices at their ends to accommodate different sized users or to aid in positioning the garment 10 such that specific areas of a user's body 12 are heated by the garment 10.

In the preferred embodiment, the healing garment 10 is constructed of a cloth material. Preferably, the cloth material is a sanded twill material that is durable and generally comfortable for a user. The healing garment 10 is not limited to constructions utilizing cloth material or sanded twill material and may be constructed of nearly any material that permits a user to position the healing garment 10 on the user's body 12 with a level of comfort and is structurally adequate to perform the tasks of the garment 10, described in greater detail below. For example, the healing garment 10 may be constructed of a polymeric material that is structurally sound and relatively comfortable for a user to wear.

The garment 10 also includes at least one pocket 22 on the support structure 14. In the preferred embodiment, the at least one pocket 22 includes first, second and third pockets 22a, 22b, 22c located on the first garment section 14 and a fourth pocket 22d located on the second garment section 18. Each of the pockets 22a–22d includes a mouth 24 into which at least one mass 26 is removably positionable. The at least one mass 26 is removably positionable in the pockets 22a–22d through the mouths 24. The first, second and third pockets 22a–22c have a generally U-shape and are constructed similar to a pant pocket with an open mouth 24. The first, second and third pockets 22a–22c are not limited to such constructions and may take on any shape or form that permits the first, second and third pockets 22a–22c to hold the at least one mass 26 therein. Preferably, the fourth pocket 22d is selectively sealable such that at least one mass 26 may be selectively sealed and retained within the fourth pocket 22d. However, the fourth pocket 22d is not limited to configurations in which it is selectively sealable and may include an open mouth 24 similar to the mouths 24 of the first, second and third pockets 22a–22c or may include a clip, strap or similar device that secures the mass 26 within the fourth pocket 22d without the inclusion of a selectively sealable mouth 24. Additional structures or methods for securing the mass 26 within the fourth pocket 22d will be apparent to one having ordinary skill in the art.

Preferably, the pockets 22a–22d are comprised of the same material as the support structure 14 and are attached or formed on or in the support structure 14 in a manner that is well known by one having ordinary skill in the art. However, the pockets 22a–22d are not limited to constructions including the same material of the support structure 14 and may be constructed of a different material than the support structure 14. For example, the pockets 22a–22d may be constructed of an elastic material that aids in holding the at least one mass 26 in the pockets 22a–22d in a working position while the support structure 14 is constructed of the sanded twill material that provides a comfortable feel to a user.

In the preferred embodiment, the first, second and third pockets 22a–22c are positioned on the front side of the first garment section 16. The at least one mass 26 and/or other objects are inserted into one or all of the first, second and third pockets 22a–22c through the mouth 24 and are generally held within the first, second and third pockets 22a–22c by the force of gravity. However, as was described above, the pockets 22a–22c may be constructed of an elastic material that may permit the mouth 24 to be located on a side or bottom of the pockets 22a–22c such that the at least one mass 26 is held therein by the elastic force, despite the force of gravity. In addition, the first, second and third pockets 22a–22c are not limited to locations on the front side of the support structure 14 and may be positioned within the support structure 14 or may be located on a rear side of the support structure 14 such that the first, second and third pockets 22a–22c come into directed contact with a user's body 12 when in a working position.

In the preferred embodiment, the fourth pocket 22d has a generally arcuate rectangular shape that covers a central portion of the second garment section 18. The fourth pocket 22d is preferably formed within a central area of the second garment section 18 and is selectively sealable using an adhesive band 21 that is located adjacent an inner edge of the mouth 24 of the fourth pocket 22d. The adhesive band 21 is used to seal the at least one heated mass 26 within the fourth pocket 22d during use, because the fourth pocket 22d may be positioned in an inverted orientation in the preferred configuration. For example, when the preferred hoop-shaped support structure 14 is positioned around a user's neck 12a (FIG. 2), the mouth 24 of the fourth pocket 22d may be inverted relative to or positioned generally parallel to the ground such that the at least one mass 26 may fall out of its mouth 24 under the force of gravity. The adhesive band 21 may be opened to accept the at least one mass 26 into the pocket 22d and may also be sealed in a working position to seal the at least one mass 26 in the fourth pocket 22d during use. Similar to the above-described strips 19a–19d, 20a, 20b, the adhesive band 21 is preferably comprised of a hook and loop material, but is not so limited. The adhesive band 21 may be comprised of any number of alternate sealing methods or materials, similar to those described above for the strips 19a–19d, 20a, 20b. Further, the fourth pocket 22d is not limited to inclusion of the adhesive band 21 and may be constructed similar to the first, second and third pockets 22a–22c, having an open mouth 24. In such a construction, the fourth pocket 22d would preferably be positioned on the second garment section 18 such that the at least one mass 26 is held within the fourth pocket 22d by the force of gravity when in the working position.

In the preferred embodiment, the at least one mass 26 is comprised of at least one heated stone 26, or, specifically, at least one heated basalt stone 26. In addition, in the preferred embodiment, the at least one mass 26 is comprised of a plurality of masses 26 that are selectively positionable within the pockets 22a–22d. An individual or multiple stones 26 may be inserted in any one or more of the pockets 22a–22d, depending upon user preferences. The basalt stones 26 are generally well suited for the healing garment 10 due to their size and their ability to hold large amounts of heat energy and transfer that heat energy into the support structure 14 and, consequently, into the user's body 12 when in the working position. The basalt stones 26 are smooth volcanic rocks that, when heated and positioned adjacent a user's body 12, transmit heat energy into the body 12 and relax muscles and/or improve energy flow. The heated masses 26 are not limited to stones and/or basalt stones 26 and may be comprised of any mass that is able to retain heat, be positioned within one of the pockets 22a–22d and transmit heat energy through the support structure 14 to the user's body 12. For example, the at least one heated mass 26 may be comprised of a fluid filled package (not shown) that retains heat, is positionable in one of the pockets 22a–22d and transmits heat energy into the support structure 14.

The preferred healing garment 10 further includes a sleeve 28 that is positioned on a front of the second pocket 22b and removably receives a mineral mass 30. The preferred sleeve 28 has a generally heart-shape and is a constructed similar to a conventional pant pocket that is positioned on the front of the second pocket 22b. The mineral mass 30 is preferably comprised of a gemstone that increases the energy of all of the heated masses or basalt stones 26 during use and is preferably comprised of a unakite stone 30. The use of the unakite stone 30 is not meant to be limiting but is preferred to increase the energy of the heated masses 26 and improve relaxation and energy flow in the user's body 12 when the garment 10 is in the working position. The mineral mass 30 may be comprised of any gemstone or mass that is positionable in the sleeve 28 and increases the energy of the heated masses 26 during use. In addition, the mineral mass 30 is not limited to being positioned in the sleeve 28 and may be located anywhere near or on the support structure 14, for example, in one of the pockets 22a–22d, such that the energy of the heated masses 26 are increased during use.

The preferred garment 10 permits the alteration of the size of the hole 32 in the center of the support structure 14 to accommodate different sized users or to position the pockets 22a–22d adjacent different parts of a user's body 12. For example, the smallest hole 32 is created in the preferred support structure 14 when the first securing strip 19a on the first end 16a is attached to the fifth securing strip 20a on the third end 18a and the third securing strip 19c on the second end 16b is attached to the sixth securing strip 20b on the fourth end 18b. In contrast, the largest hole 32 is created in the preferred support structure 14 when the second securing strip 19b on the first end 16a is attached to the fifth securing strip 20a on the third end 18a and the fourth securing strip is attached to the sixth securing strip 20b on the fourth end 18b. The garment 10 is not limited to the specific number of securing strips 19a–19d, 20a, 20b, shown in the preferred embodiment, and may include additional securing strips or extensions to accommodate different sized users and/or to position the pockets 22a–22d at different locations on the user's body 12.

In operation, the basalt stones 26, are heated to a predetermined temperature and are inserted into one or more of the respective pockets 22a–22d through their mouths 24. Referring to FIG. 2, the first garment section 16 is placed on the chest 12b of the user's body 12 such that the first, second, third and fourth securing strips 19a–19d adjacent the first and second ends 16a, 16b are positioned between the user's shoulder 12c and neck 12a. The second garment section 18 is then secured to the first garment section 16 at the first and third ends 16a, 18a and second and fourth ends 16b, 18b using one of a pair of securing strips 19a–19d, 20a, 20b. The first and second garment sections 16, 18 are secured relative to each other and relative to the user's body 12 such that the pockets 22a–22d are located adjacent the chest 12b and neck 12a. Heat energy from the heated basalt stones 26 is transferred through the healing garment 10 to the user's body 12 adjacent the pockets 22a–22d to enhance relaxation and improve energy flow. The healing garment 10 is particularly well suited for users who are receiving a pedicure and/or manicure such that the user receives a full body treatment at the same time as the pedicure and/or manicure. However, the garment 10 is not limited to pedicure and/or manicure uses and may be used in nearly any situation, for example, during a massage or in a user's home to enhance relaxation and improve energy flow.

In the preferred embodiment, the basalt stones 26 are heated in a pool of heated water to a temperature of approximately one hundred twenty degrees Fahrenheit (120° F.). The stones 26 are then dried and positioned within one of the pockets 22a–22d through one of the mouths 24. Preferably, a plurality of basalt stones 26 are positioned in the fourth pocket 22d of the second garment section 18. The plurality of basalt stones 26 are positioned in the fourth pocket 22d such that the pocket 22d is filled with the stones 26 and an entire area behind the user's neck 12a and adjacent the back of a user's shoulders 12c receive heat energy from the stones 26 when in the working position. The stones 26 in the fourth pocket 22d are sealed in the pocket 22d by pressing the inner edges of the mouth 24 together, thereby securing one side of the adhesive band 21 to the opposite side of the adhesive band 21. In the working position, the first, second and third pockets 22a–22c of the first garment section 16 are positioned adjacent the user's heart and the user's collar bones. Positioning of the first, second and third pockets 22a–22c in the above-described positions provide healing to these areas through the transfer of heat energy from the stones 26.

Referring to FIGS. 1–3, in the preferred embodiment, the unakite stone 30 is positioned in the heart-shaped sleeve 28 during use. The unakite stone 30 increases the energy of all of the heated masses 26 to enhance the relaxation of and improve energy flow through the user's body 12. The insertion of the unakite stone 30 into the sleeve 28 is not meant to be limiting but is preferred to increase the energy of the heated masses 26 and improve relaxation of the user.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A garment for warming, cooling or maintaining the temperature of a specific area of a user's body comprising:
    a hoop-shaped support structure including a first garment section and a second garment section;
    at least one pocket on each of the first and second garment sections; and
    at least one mass, the mass being removably positionable in one pocket, the garment being worn by a user such that the at least one pocket on the first garment section is adapted to be positioned proximate a user's collarbone and the at least one pocket on the second garment section is adapted to be positioned proximate a back of the user's neck above the shoulder blades in a working position.

2. The garment of claim 1 wherein the first garment section includes first and second ends and the second garment section includes third and fourth ends, the first and third ends and the second and fourth ends being removably securable to each other.

3. The garment of claim 2 wherein a hook and loop material is secured to the first and second garment sections at the first, second, third and fourth ends.

4. The garment of claim 3 wherein the first and second garment sections are securable to each other at the first and third ends and the second and fourth ends using the hook and loop material.

5. The garment of claim 2 wherein the at least one pocket includes first, second and third pockets located on the first garment section and a fourth pocket located on the second garment section, the fourth pocket being selectively sealable.

6. The garment of claim 5 wherein the fourth pocket is selectively sealable using a hook and loop material located adjacent a mouth of the fourth pocket.

7. The garment of claim 1 further comprising:
    a sleeve; and
    a mineral mass removably positionable in the sleeve.

8. The garment of claim 7 wherein the mineral mass is a unakite stone.

9. The garment of claim 1 wherein the at least one mass is comprised of a heated or cooled stone.

10. The garment of claim 1 wherein the at least one mass is comprised of a basalt stone.

11. The garment of claim 1 wherein the support structure and at least one pocket are constructed of a cloth material.

12. The garment of claim 11 wherein the cloth material is a sanded twill material.

* * * * *